United States Patent [19]
Stock

[11] Patent Number: 5,696,379
[45] Date of Patent: Dec. 9, 1997

[54] MEASURING APPARATUS FOR MEASURING THE CONCENTRATION OF GASES UTILIZING INFRARED ABSORPTION

[75] Inventor: Burkhard Stock, Lübeck, Germany

[73] Assignee: Dr ägerwerk AG, Lübeck, Germany

[21] Appl. No.: 660,177

[22] Filed: Jun. 3, 1996

[30] Foreign Application Priority Data

Jun. 3, 1995 [DE] Germany ............ 195 20 488.3

[51] Int. Cl.⁶ ............................................... G01J 21/61
[52] U.S. Cl. ............................................... 250/343
[58] Field of Search ................................... 250/343

[56] References Cited

U.S. PATENT DOCUMENTS 4,228,352  10/1980  Adrian ............................ 250/343
5,341,214   8/1994  Wong .............................. 356/437
5,384,640   1/1995  Wong .............................. 356/437

FOREIGN PATENT DOCUMENTS 2650350  5/1978  Germany .

Primary Examiner—Constantine Hannaher
Attorney, Agent, or Firm—Walter Ottesen

[57] ABSTRACT

A measuring apparatus for measuring the concentration of a gas by infrared absorption includes a first radiation source 11 having a first modulation frequency, an arcuate waveguide 13 for receiving the gas to be measured therein, and two radiation detectors (15, 16). The measuring apparatus of the invention is a compact gas measuring apparatus having a simple configuration. The temperature dependent and deterioration dependent changes of the two radiation detectors (15, 16) are compensated. A second radiation source 12 having a second modulation frequency is mounted between the first radiation source 11 and the radiation detectors (15, 16).

10 Claims, 2 Drawing Sheets

MEASURING APPARATUS FOR MEASURING THE CONCENTRATION OF GASES UTILIZING INFRARED ABSORPTION

BACKGROUND OF THE INVENTION

A measuring apparatus for measuring the concentration of gases utilizing infrared absorption is disclosed in German published patent application 2,650,350. With an arrangement of this kind, it is intended to provide a compact gas analysis apparatus. It is also intended to omit complex adjustments for additional optical components, such as mirrors, because the propagation of light via multiple reflections within a curved waveguide can be utilized for the measurement at the end of the beam path. In this known arrangement, neither the dependency on temperature nor the dependency on deterioration of the measuring and reference detectors is compensated.

SUMMARY OF THE INVENTION

It is an object of the invention to provide a compact simply assembled gas measuring device wherein temperature dependent changes and deterioration dependent changes on the measurement and reference detectors are compensated.

The measuring apparatus of the invention is for measuring the concentration of a gas by infrared absorption. The measuring apparatus includes: a hollow waveguide defining a measuring length and an interior for receiving the gas to be measured; a first radiation source for emitting infrared radiation; a second radiation source for emitting infrared radiation; first and second radiation detectors for converting the infrared radiation into first and second measurement quantities; and, means for distinguishing the first measurement quantity from the second measurement quantity.

The significant advantage of the invention is that a compact arrangement for measuring the concentration of gases with the aid of infrared absorption is provided wherein deterioration drift and temperature drift of the detectors utilized are compensated. Also, a simple and robust assembly is made possible because of a reduction of the otherwise conventional number of optical components.

The measuring arrangement for determining the concentration of gases via infrared absorption includes a waveguide for receiving the gas to be measured therein. The waveguide constitutes the measuring path and the measuring apparatus further includes a first infrared radiation source and measurement and reference detectors. These detectors convert emitted radiation into a first measurement variable which is preferably electrical. In addition, a second infrared radiation source is provided which generates a second measurement variable at the radiation detectors with this measurement variable being preferably likewise electrical. Means are provided for distinguishing the first measurement variable from the second measurement variable.

The assembly of the apparatus is, as a rule, realized in that no additional mirrors are used and that both radiation sources are disposed within the waveguide. It is, however, also possible to mount the first infrared radiation source outside of the waveguide. In this case, the light of the first radiation source would be imaged via one or several suitable mirrors onto the cross-sectional area of the waveguide so that the image of the first radiation source is greatly defocused because of the subsequent reflections in the waveguide having the gas which is disposed therein and is to be measured. The cross-sectional area of the waveguide is closed off with a window and the waveguide itself is configured as a curved tube. The second infrared radiation source can, in this case, be disposed directly on the other side of the window, that is, in the interior space of the waveguide. In general, the gas to be measured enters via openings into the waveguide. Two radiation detectors are, as a rule, used and are located at opposite end of the waveguide.

Alternatively, the light of the second radiation source can be apportioned to the detectors via a beam splitter at the opposite end of the waveguide, for example, via an appropriately positioned semi-transmitting mirror which simultaneously functions as the entrance surface for the light of the second radiation source (that is, to couple in the light of the second radiation source). The semi-transmitting mirror is in this case so positioned that the light from each radiation source is divided into two halves with the halves being transmitted to the detectors, respectively, in that these detectors are for example mounted at right angles to each other with the mirror being disposed symmetrically therebetween.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
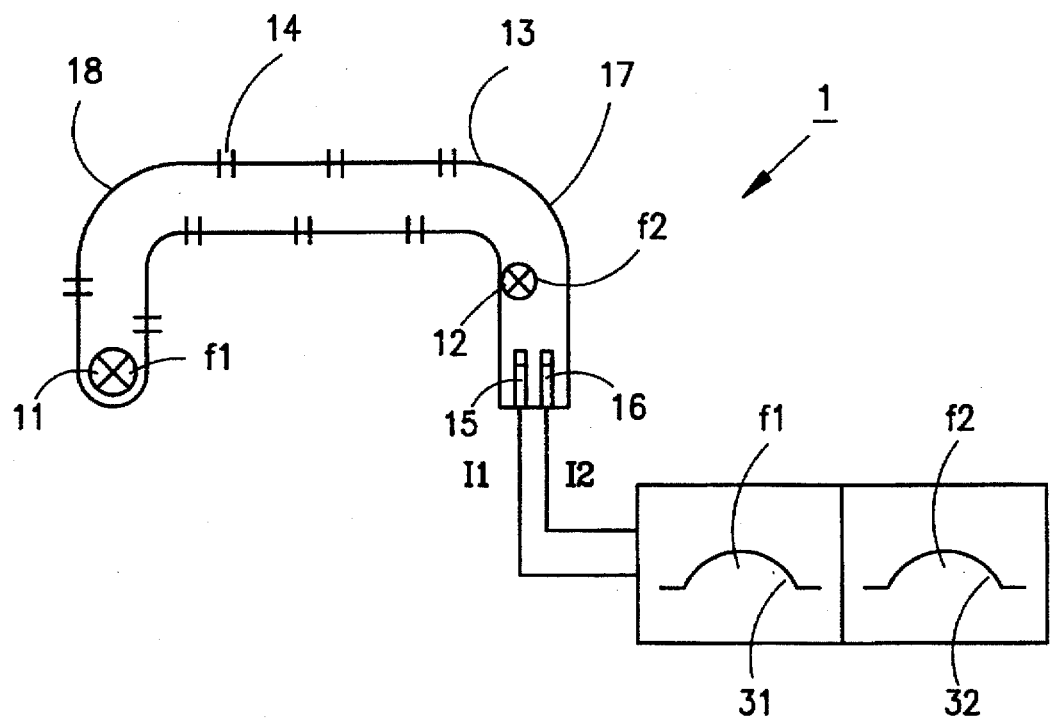
FIG. 1 is a schematic of a first embodiment of the apparatus according to the invention.

The apparatus of the invention shown in FIG. 1 is identified by reference 1 and includes a waveguide 13 which, in this embodiment, also defines the gas measuring cell. The gas to be measured flows through the inlets 14 into the waveguide 13.

In the simplest embodiment, the waveguide 13 is a metal tube or a tube which is mirrored on the inside. The tube has a circular cross section and includes two segments (17, 18) curved at 90° so that the beam from the radiation source 11 is deflected twice by 90° along the path to the detectors (15, 16).

In lieu of two deflections as shown, an arcuate tube section defining a semi-circular path is also conceivable. What is decisive is that the infrared light, which is radiated by the radiation source 11, impinges on the detectors (15, 16) after several reflections. The image of the radiation source 11 is greatly defocused because the waveguide 13 is arcuate.

The variation of the intensity over the cross-sectional area of the waveguide 13 at the location of the detectors (15, 16) is quite flat and therefore exhibits only a very slight dependency upon the spatial position of the radiation source 11.

This is in contrast to the course of the radiation in a straight tube conductor which is conventionally used and wherein the structure of the imaged radiation source is still sharply retained and the intensity of the imaging in the center has a maximum and drops off greatly toward the edges.

From the foregoing, the requirement results for a very stable mechanical configuration of a conventional linear measuring arrangement. It is especially critical when the radiation source is imaged via beam splitters onto, for example, two detectors of which one functions as a reference to eliminate deterioration of the radiation source.

The light is apportioned in a different manner onto the reference and measuring detectors when the image of the radiation source shifts because of mechanical influences or because of geometric changes. This can cause errors in the measurement of the gas concentration. In practice, the waveguide 13 should not be too thin because, otherwise, the number of wall reflections will greatly increase and the intensity of the measured signals will become less because of reflection losses. The ratio of the length L to the diameter D should be L/D<30 and the radius of curvature should not be greater than three times the diameter in order to obtain the desired defocusing.

For an optimal light yield, the diameter of the waveguide 13 should correspond to the detector size (15, 16). For the practical application, a waveguide diameter in the range of 5 to 15 mm results from these requirements.

According to the invention, a second radiation source 12 is used to compensate for the different temperature drift and the different course of deterioration of the measurement and reference detectors (15, 16). The two radiation sources (11, 12) are modulated at different frequencies ($f_1$, $f_2$), for example, at 2 and 3.7 Hz or at 11 and 17 Hz. The light of the radiation source 12 functions to standardize measurement and reference detectors (15, 16); whereas, the light of the radiation source 11 functions to measure the gas concentration. The different frequencies of the detector signals can again be separated by suitable evaluation methods known from the state of the art.

A first measurement variable 31 for a first modulation frequency $f_1$ and a second measurement variable 32 for a second modulation frequency $f_2$ are obtained as a result of the measurement.

According to another embodiment of the invention, the hollow waveguide 13 can be curved in more than one plane.

Figure 2:
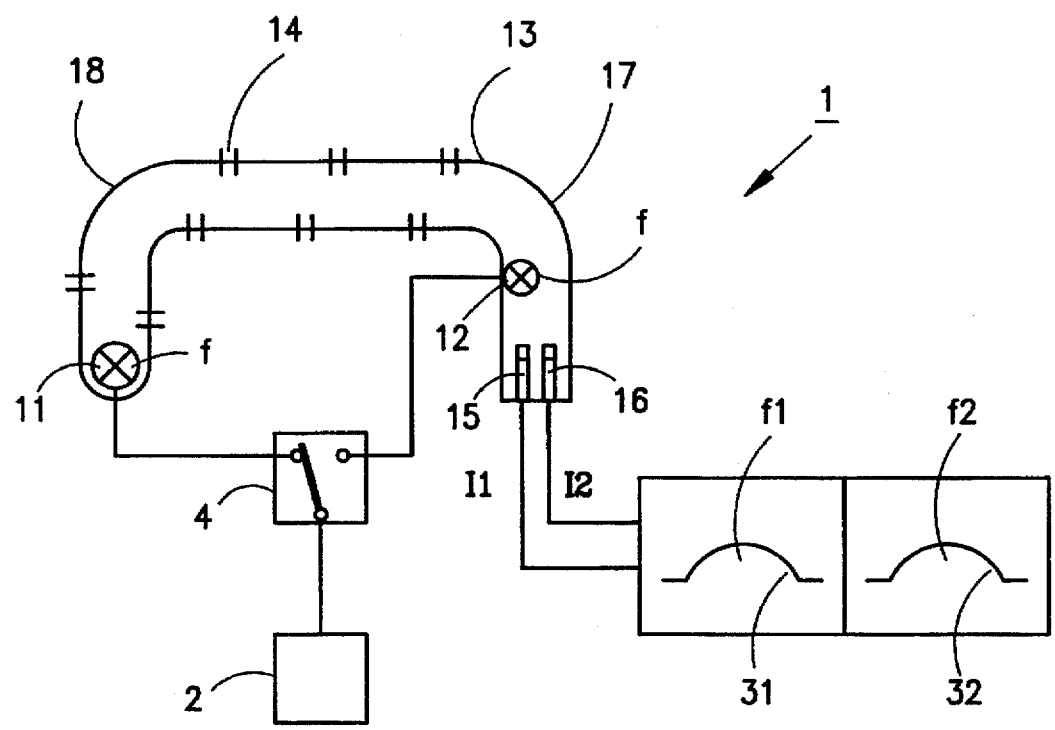
FIG. 2 is a schematic of a second embodiment of the apparatus of the invention wherein the radiation sources are energized alternately utilizing a switch; and, FIG. 3 shows a third embodiment of the apparatus of the invention wherein different cuvettes are used with one and the same measuring apparatus.

According to another embodiment shown in FIG. 2, the two lamps are driven at the same frequency but are alternately switched on and off, for example, lamp 11, 30 seconds on, lamp 12 out; lamp 11 out, lamp 12, 30 seconds on, et cetera. A current supply 2 provides a supply current at frequency f to a switch 4 which switches the supply current between the two lamps 11 and 12.

Figure 3:
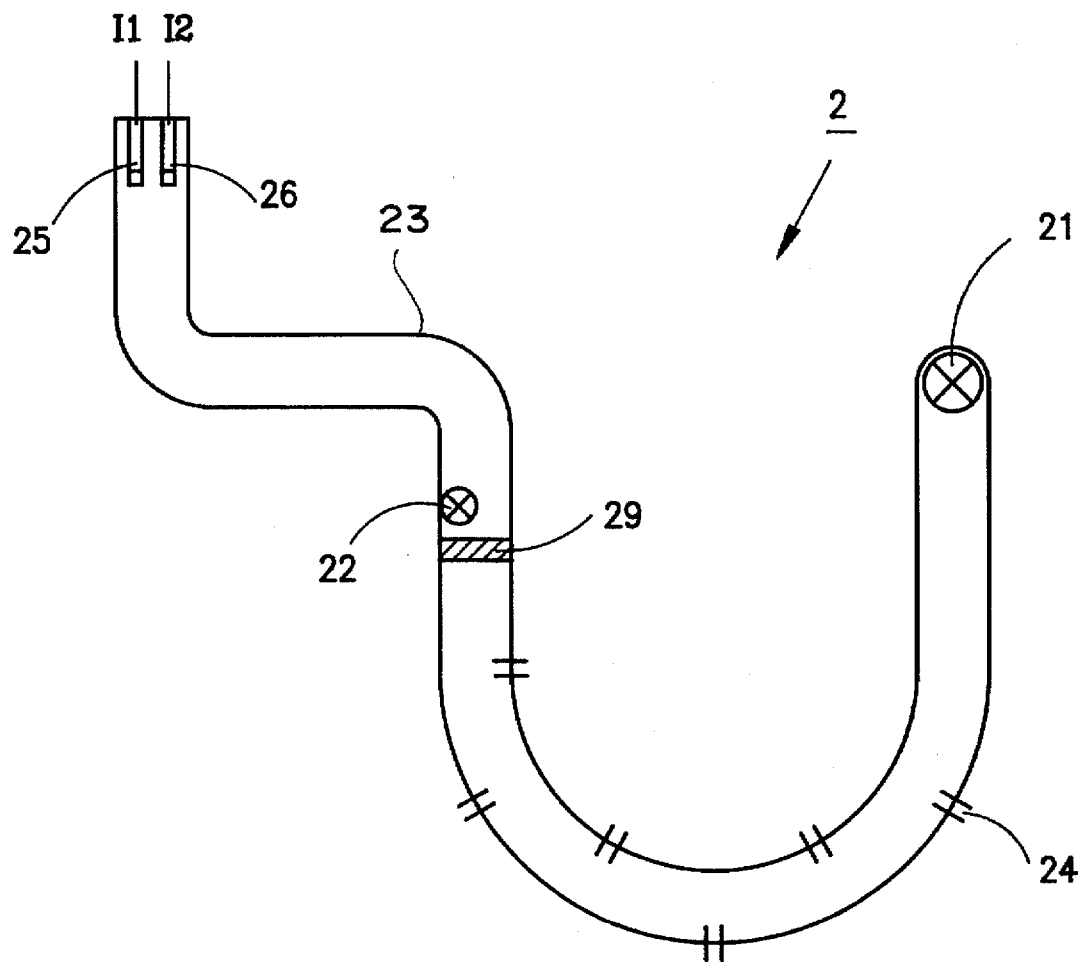

Still another embodiment of the invention is shown in FIG. 3 wherein different measuring cuvettes are used with one and the same measuring apparatus. In the embodiment shown, a window 29 is additionally provided so that the gas to be measured is disposed in the segment forward thereof and up to the first radiation source 21. The gas to be measured flows through inlets 24 into the waveguide. The component device is closed off by the detectors (25, 26) at the one end and the window 29 at the other end. This component device can, for example, be combined also with different measuring cuvettes having a radiation source 21, for example, as a reduced radiator or in combination with a concave mirror.

In each case, the radiation source 21 is imaged on the entry opening (window 29) of the arcuate waveguide 23. The intensity distribution of the light from the radiation source 21 is made uniform over the cross section in the detector plane by the curvature of the waveguide.

It is understood that the foregoing description is that of the preferred embodiments of the invention and that various changes and modifications may be made thereto without departing from the spirit and scope of the invention as defined in the appended claims.

What is claimed is:

1. A measuring apparatus for measuring the concentration of a gas by infrared absorption, the measuring apparatus comprising:

a hollow waveguide defining a measuring length and an interior for receiving the gas to be measured;

a first radiation source for emitting infrared radiation;

a second radiation source for emitting infrared radiation;

first and second radiation detectors for converting said infrared radiation into first and second measurement quantities; and, said first radiation source being adapted to emit infrared radiation modulated at a first modulation frequency and said second radiation source being adapted to emit infrared radiation modulated at a second modulation frequency.

2. The measuring apparatus of claim 1, said hollow waveguide being curved in more than one plane.

3. The measuring apparatus of claim 1, wherein: said hollow waveguide has a predetermined length (L) and a predetermined diameter (D); and, a ratio of said length (L) to said diameter (D) is less than 30.

4. The measuring apparatus of claim 1, wherein: said hollow waveguide has a radius (R) of curvature and a diameter (D); and, a ratio of said radius (R) of curvature to said diameter (D) is less than 3.

5. A measuring apparatus for measuring the concentration of a gas by infrared absorption, the measuring apparatus comprising:

a hollow waveguide defining a measuring length and an interior for receiving the gas to be measured;

a first radiation source for emitting infrared radiation;

a second radiation source for emitting infrared radiation;

first and second radiation detectors for converting said infrared radiation into first and second measurement quantities;

a current supply for supplying current for energizing said radiation sources; and, switching means for alternately connecting said current supply to said first radiation source and said second radiation source.

6. The measuring apparatus of claim 5, said hollow waveguide being curved in more than one plane.

7. The measuring apparatus of claim 5, said first and second radiation sources being spaced apart along said hollow waveguide; said hollow waveguide defining an enclosed space between said first and second radiation sources for receiving said gas therein; and, a window impermeable to said gas and mounted in said hollow waveguide for partitioning said enclosed space and said gas from said second radiation source and said detectors.

8. The measuring apparatus of claim 5, wherein: said hollow waveguide has a predetermined length (L) and a predetermined diameter (D); and, a ratio of said length (L) to said diameter (D) is less than 30.

9. The measuring apparatus of claim 5, wherein: said hollow waveguide has a radius (R) of curvature and a diameter (D); and, a ratio of said radius (R) of curvature to said diameter (D) is less than 3.

10. A measuring apparatus for measuring the concentration of a gas by infrared absorption, the measuring apparatus comprising:

a hollow waveguide defining a measuring length and an interior for receiving the gas to be measured;

a first radiation source for emitting infrared radiation;

a second radiation source for emitting infrared radiation;

first and second radiation detectors for converting said infrared radiation into first and second measurement quantities;

said first radiation source being adapted to emit infrared radiation modulated at a first modulation frequency and said second radiation source being adapted to emit infrared radiation modulated at a second modulation frequency;

said first and second radiation sources being spaced apart along said hollow waveguide;

said hollow waveguide defining an enclosed space between said first and second radiation sources for receiving said gas therein; and, a window impermeable to said gas and mounted in said hollow waveguide for partitioning said enclosed space and said gas from said second radiation source and said detectors.

* * * * *